(12) United States Patent
Hunter et al.

(10) Patent No.: US 6,474,341 B1
(45) Date of Patent: Nov. 5, 2002

(54) SURGICAL COMMUNICATION AND POWER SYSTEM

(75) Inventors: Mark W. Hunter, Broomfield, CO (US); Paul Kessman, Broomfield, CO (US); Brad Jascob, Broomfield, CO (US)

(73) Assignee: Surgical Navigation Technologies, Inc., Louisville, CO (US)

( * ) Notice: Subject to any disclaimer, the term of this patent is extended or adjusted under 35 U.S.C. 154(b) by 0 days.

(21) Appl. No.: 09/428,722

(22) Filed: Oct. 28, 1999

(51) Int. Cl.[7] .............................................. A61B 19/00
(52) U.S. Cl. ...................................................... 128/899
(58) Field of Search ........................ 128/899; 600/300, 600/301, 549, 509; 607/32; 340/10.6; 324/652

(56) References Cited

U.S. PATENT DOCUMENTS

| | | |
|---|---|---|
| 3,868,565 A | 2/1975 | Kuipers |
| 4,182,312 A | 1/1980 | Mashabac |
| 4,314,251 A | 2/1982 | Raab |
| 4,317,078 A | 2/1982 | Weed et al. |
| 4,339,953 A | 7/1982 | Iwasaki |
| 4,399,441 A * | 8/1983 | Vaughan et al. ............ 600/549 |
| 4,422,041 A | 12/1983 | Lienau |
| 4,431,005 A | 2/1984 | McCormick |
| 4,618,978 A | 10/1986 | Cosman |
| 4,642,786 A | 2/1987 | Hansen |
| 4,722,056 A | 1/1988 | Roberts et al. |
| 4,737,794 A | 4/1988 | Jones |
| 4,793,355 A | 12/1988 | Crum et al. |
| 4,821,731 A | 4/1989 | Martinelli et al. |
| 4,905,698 A | 3/1990 | Strohl, Jr. et al. |
| 5,057,095 A | 10/1991 | Fabian |
| 5,160,337 A | 11/1992 | Cosman |
| 5,186,174 A | 2/1993 | Schlöndorff et al. |
| 5,187,475 A | 2/1993 | Wagener et al. |
| 5,198,877 A | 3/1993 | Schulz |

(List continued on next page.)

FOREIGN PATENT DOCUMENTS

| | | |
|---|---|---|
| EP | 0 655 138 B1 | 4/1998 |
| EP | 0 894 473 A2 | 2/1999 |
| WO | WO 94/04938 | 3/1994 |
| WO | WO 00/69335 | 11/2000 |

OTHER PUBLICATIONS

Schreiner, S., et al. "An Ultrasonic Approach to Localization of Fiducial Markers for Interactive, Image–Guided Neurosurgery–Part II: Implementation and Automation" IEEE Transactions on Biomedical Engineering, IEEE, Inc. New York, vol. 45, No. 5; May 1, 1998, pp. 631–641, XP–000740789; ISSN: 0018–9294 the whole document.

*Primary Examiner*—Kevin Shaver
*Assistant Examiner*—Brian Szmal
(74) *Attorney, Agent, or Firm*—Harness, Dickey & Pierce, P.L.C.

(57) ABSTRACT

An apparatus for determining the position of a wireless catheter probe being used during a surgical procedure. Magnetic fields are projected into an anatomical body to induce voltage signals in a sensing coil that are sufficient to describe the position of a wireless sensor/transmitter. The voltage signals are wirelessly re-transmitted by the sensor/transmitter as positional signals indicative of a current location of the sensor/transmitter in the anatomical body. In a preferred embodiment, the wireless catheter probe is self-powered using the induced voltage signals on a sensing coil. In another embodiment, induced voltage signals of a separate coil are used to power the device.

20 Claims, 6 Drawing Sheets

U.S. PATENT DOCUMENTS

| | | |
|---|---|---|
| 5,715,822 A | 2/1998 | Watkins et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,738,096 A | 4/1998 | Ben-Haim |
| 5,744,953 A | 4/1998 | Hansen |
| 5,748,767 A | 5/1998 | Raab |
| 5,749,835 A | 5/1998 | Glantz |
| 5,752,513 A | 5/1998 | Acker et al. |
| 5,752,976 A * | 5/1998 | Duffin et al. ............ 607/32 |
| 5,755,725 A | 5/1998 | Druais |
| RE35,816 E | 6/1998 | Schultz |
| 5,758,667 A | 6/1998 | Slettenmark |
| 5,762,064 A | 6/1998 | Polvani |
| 5,769,843 A | 6/1998 | Abela et al. |
| 5,769,861 A | 6/1998 | Vilsmeier |
| 5,782,765 A | 7/1998 | Jonkman |
| 5,787,886 A | 8/1998 | Kelly et al. |
| 5,797,849 A | 8/1998 | Vesely et al. |
| 5,800,352 A | 9/1998 | Ferre et al. |
| 5,810,728 A | 9/1998 | Kuhn |
| 5,823,958 A | 10/1998 | Truppe |
| 5,829,444 A | 11/1998 | Ferre et al. |
| 5,833,608 A | 11/1998 | Acker |
| 5,836,954 A | 11/1998 | Heilbrun et al. |
| 5,840,025 A | 11/1998 | Ben-Haim |
| 5,848,967 A | 12/1998 | Cosman |
| 5,851,183 A | 12/1998 | Bucholz |
| 5,871,445 A | 2/1999 | Bucholz |
| 5,871,455 A | 2/1999 | Ueno |
| 5,873,822 A | 2/1999 | Ferre et al. |
| 5,882,304 A | 3/1999 | Ehnholm et al. |
| 5,884,410 A | 3/1999 | Prinz |
| 5,891,034 A | 4/1999 | Bucholz |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,938,603 A | 8/1999 | Ponzi |
| 5,947,981 A | 9/1999 | Cosman |
| 5,971,997 A | 10/1999 | Guthrie et al. |
| 6,025,725 A * | 2/2000 | Gershenfeld et al. ....... 324/652 |

* cited by examiner

SURGICAL COMMUNICATION AND POWER SYSTEM

CONCURRENTLY FILED APPLICATIONS

The following United States patent applications, which were concurrently filed with this one on Oct. 28, 1999, are fully incorporated herein by reference: Method and System for Navigating a Catheter Probe in the Presence of Field-influencing Objects, by Michael Martinelli, Paul Kessman and Brad Jascob; Patient-shielding and Coil System, by Michael Martinelli, Paul Kessman and Brad Jascob; Navigation Information Overlay onto Ultrasound Imagery, by Paul Kessman, Troy Holsing and Jason Trobaugh; Coil Structures and Methods for Generating Magnetic Fields, by Brad Jascob, Paul Kessman and Michael Martinelli; Registration of Human Anatomy Integrated for Electromagnetic Localization, by Mark W. Hunter and Paul Kessman; System for Translation of Electromagnetic and Optical Localization Systems, by Mark W. Hunter and Paul Kessman; and Surgical Sensor, by Mark W. Hunter, Sheri McCoid and Paul Kessman.

BACKGROUND OF THE INVENTION

A. Field of the Invention

The present invention relates to wireless remote medical devices. The invention has particular application when used with a method and system for determining the position of a wireless catheter probe being used during a surgical procedure.

B. Description of the Related Art

Various locating systems have been used in the past to determine the position of an object such as the tip of an endoscope or a catheter within the human body.

Systems and methods are known for determining the location of a catheter or endoscopic probe inserted into a selected body cavity of a patient undergoing a surgical procedure. For example, there exist systems that may use acoustics, optics, conductance and electromagnetics to locate or "localize" a medical instrument in an anatomical body. In an electromagnetic system, location data may be obtained from electrical measurements of voltage signals that are induced within a sensing coil affixed to the distal end of the catheter prove. A voltage is induced in the sensing coil in response to pre-specified electromagnetic fields that project into the anatomical region of interest which contains all prospective locations of the catheter probe. The electrical measurements of the induced signals may provide sufficient information to compute the angular orientation and the positional coordinates of a coil in a sensor, and hence the catheter probe, which collectively define the location of the coil.

Regardless of the technical particulars of a surgical localization system, each system typically includes a component internal to the patient associated with a medical device and a component external to the patient for calculating the position of the medical instrument.

SUMMARY OF THE INVENTION

The present invention is directed to improving communication links between internal and external surgical navigation components and to providing wireless power to internal components.

The invention in its broadest sense may include one or more of the following aspects alone or in combination with one or more elements:

an apparatus and method for locating a wireless sensor/transmitter within an anatomical body, at least one signal generator for sending reference signals through the anatomical body to be received by the sensor/transmitter and to be wirelessly re-transmitted by the sensor/transmitter as positional signals indicative of a current location of the sensor/transmitter in the anatomical body, a receiver for receiving positional signals from the wireless sensor/transmitter, a processor for computing a position of a wireless sensor/transmitter as a function of the positional signals transmitted to a receiver, and a circuit associated with the processor for outputting position image information to a display device, a wireless sensor/transmitter for use in surgical procedures to track the movement of structures within an anatomical body having a portion for receiving a reference signal from a reference signal generator, and a portion for wirelessly transmitting the reference signal as a positional signal indicative of a current position of the sensor and hence the probe, a sensor having a coil adapted to have a voltage induced therein by a signal generator separated from the coil by a distance, a sensor having a circuit for powering the transmitter using an induced voltage.

It is to be understood that both the foregoing general description and the following detailed description are exemplary and explanatory only and are not restrictive of the invention, as claimed.

The accompanying drawings, which are incorporated into and constitute a part of this specification, illustrate several embodiments of the invention and together with the description, serve to explain the principles of the invention.

DESCRIPTION OF THE PREFERRED EMBODIMENTS

The present invention may be used in connection with any wireless surgical navigation system for determining a position of a medical instrument during surgery including the method and apparatus disclosed in U.S. Pat. No. 5,592,939 to Martinelli, hereby incorporated by reference. For brevity, the details of this system, including the assembly of the coils for generating a magnetic field within an anatomical body sufficient to describe the position of a medical instrument and the algorithm for determining the position of the medical instrument, are not enclosed herein.

Figure 1:
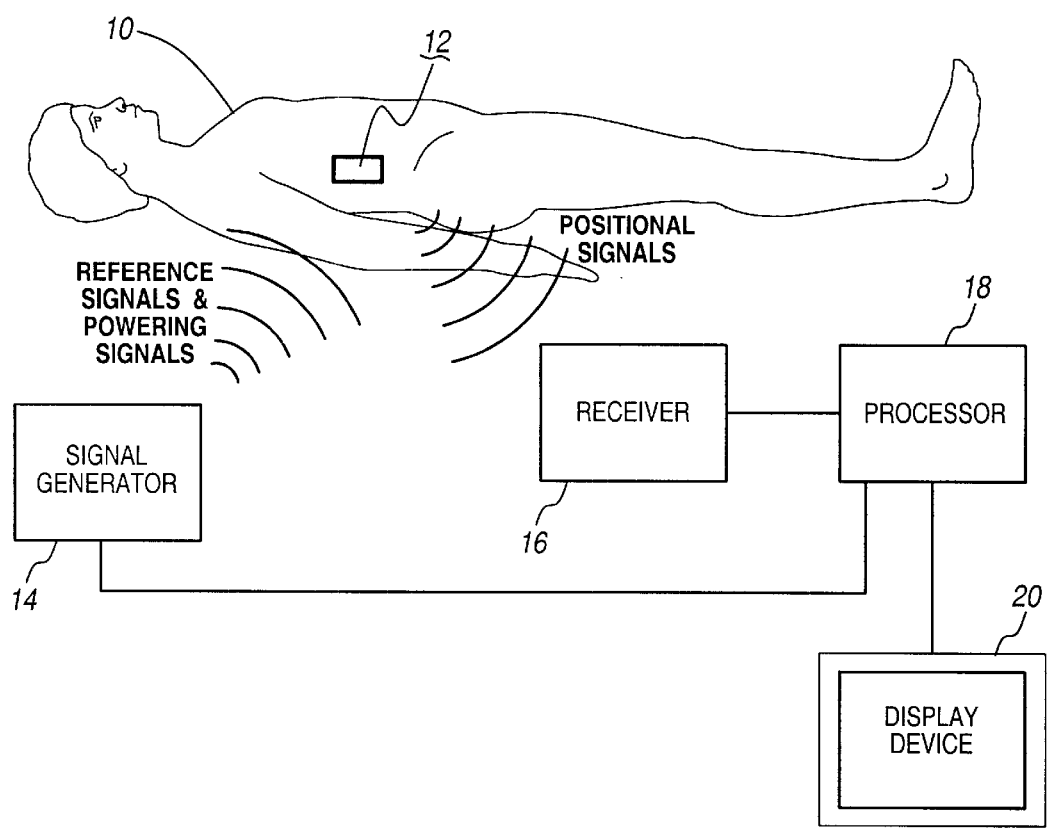
FIG. 1 is a schematic diagram of the system environment in which the features of the present invention may be implemented.

One aspect of the present invention relates to locating a wireless sensor/transmitter associated with a probe, such as a catheter, inside an anatomical body. FIG. 1 illustrates an example of the invention, where the anatomical body 10 is that of a human patient undergoing a surgical or diagnostic procedure. While a human is used in this example, the invention may be used on others such as animals. In accordance with the present invention, there is provided an apparatus for locating the position of a wireless sensor/transmitter within an anatomical body, which apparatus includes at least one signal generator for transmitting reference signals through the anatomical body to be received by the sensor/transmitter and to be wirelessly re-transmitted by the sensor/transmitter as positional signals indicative of a location of the sensor/transmitter in the anatomical body at a given instant of time.

As embodied herein, the signal generator of the invention may include at least one signal generator 14 which includes a coil capable of generating an electromagnetic field, described more fully hereinafter. As used herein, a coil refers to an electrically conductive, magnetically sensitive element of the sensor/transmitter that is responsive to time-varying magnetic fields for generating induced voltage signals as a function of, and representative of, the applied time-varying magnetic field. Preferably, signal generator 14 includes multiple coils. Each coil of the signal generator 14 may be activated in succession, each producing a magnetic field within the anatomical body 10 inducing a corresponding voltage signal in a sensing coil 22 of the sensor/transmitter 12.

In the preferred embodiment of the invention, signal generator 14 employs a distinct magnetic assembly so that the voltages induced in a sensing coil 22 corresponding to a transmitted time-dependent magnetic field produce sufficient information to describe the location, i.e. position and orientation, of the sensor/transmitter. The signals produced by the signal generator containing sufficient information to describe the position of the sensor/transmitter are referred to hereinafter as reference signals. Preferably, the reference signals are in the range of 2 KHz to 10 KHz.

Figure 2:
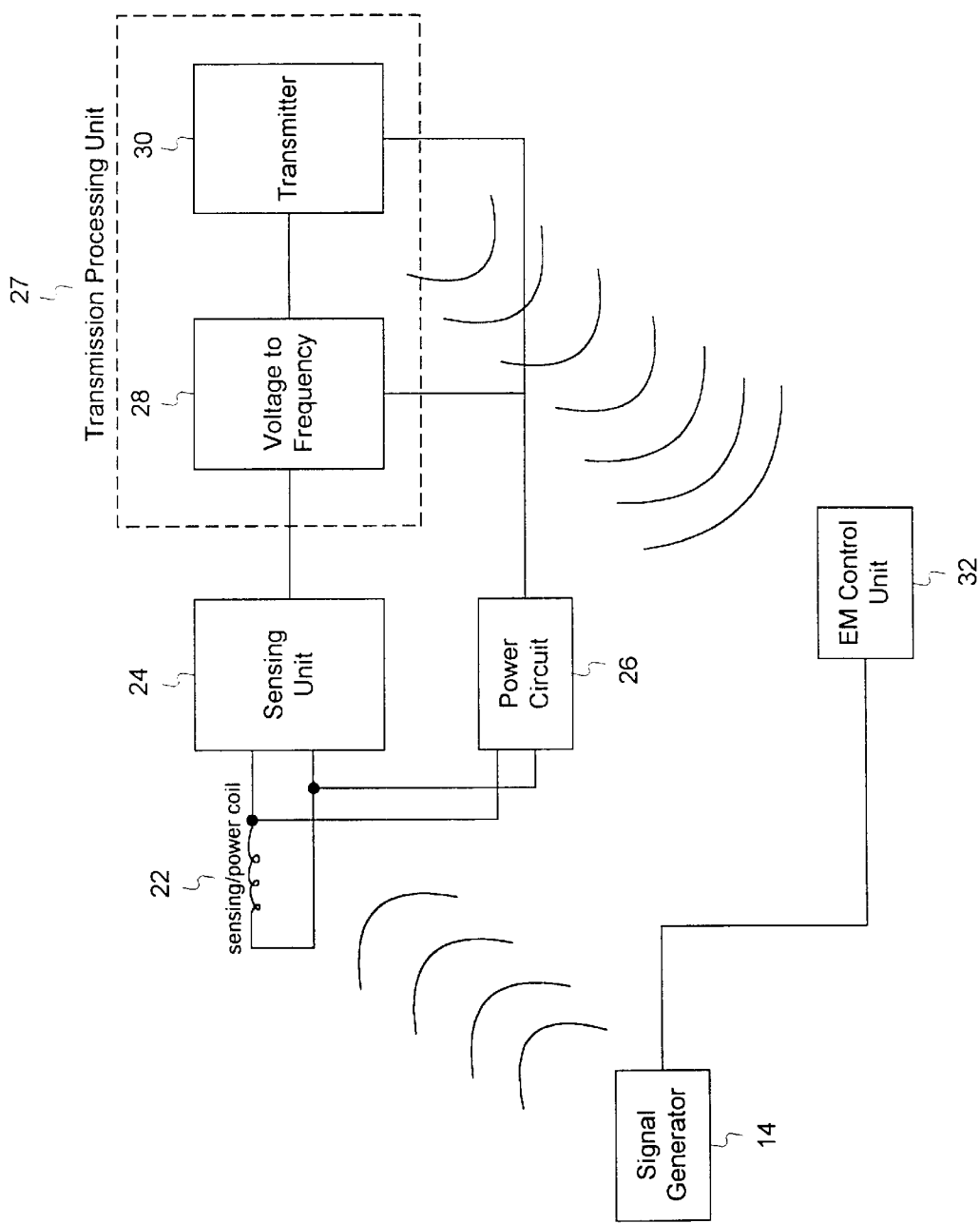
FIG. 2 is a second schematic diagram of the system environment in which the features of the present invention may be implemented.

In the preferred embodiment of the invention, the signal generator 14 is also configured to induce a voltage in the sensing coil of the sensor/transmitter sufficient to power a transmitting portion of the sensor/transmitter. In the preferred embodiment, the signals transmitted by the signal generator for powering the device, hereinafter referred to as powering signals, are frequency multiplexed with the reference signals as illustrated in FIG. 2. In the technique of frequency multiplexing, the frequency ranges of the reference signal and powering signal are modulated so as to occupy mutually exclusive frequency intervals. This technique allows the signals to be transmitted simultaneously over a common channel, such as a wireless channel, while keeping the signals apart so that they do not interfere with each other. The reference and positional signals are preferably frequency modulated (FM) for a better utilization of both power and bandwidth and an increased threshold to noise. However, amplitude modulation (AM) may also be used within the scope of the invention.

Alternatively, the powering signals may be transmitted by separate signal generators, each at a differing frequencies. Preferably, the powering signals are transmitted at higher frequencies than the reference signals. The preferred range of frequencies for the powering signals is 20 KHz to 200 KHz. Utilizing a higher modulation frequency than the reference signals enables the powering signals to couple better with the wireless sensor/transmitter, thereby enabling a greater transfer of power to the device. Using the preferred, mutually exclusive, frequency ranges for the transmission of the reference and powering signals, enables a single coil in the wireless sensor/transmitter to simultaneously receive both signals without interference of the signals.

Also in accordance with the present invention, there is provided an apparatus for locating a wireless sensor/transmitter within an anatomical body including a receiver for receiving positional signals from the wireless sensor/transmitter. As embodied herein, the receiver may include a receiver 16 that is adapted to receive radio-frequency (RF) mode positional signals or magnetic field mode positional signals.

In the preferred embodiment, the receiver 16 is adapted to receive RF signals. The RF signals may be amplitude modulated or frequency modulated signals in the frequency range of 1 MHz to 1 GHz. In the RF embodiment, there is no need to time multiplex the reference signals transmitted by the signal generator with the positional signals re-transmitted by the wireless sensor/transmitter since the signal types, magnetic and radio-frequency, are different. In other words, there is no concern with interference between the reference signal and the positional signal in the RF embodiment since the receiver 16 does not have difficulty in separating the reference signal from the positional signal.

However, a concern with interference between the reference signal and the positional signal may exist if the reference signal and the positional signal are both transmitted as a magnetic field without mutually exclusive frequency intervals. Therefore, in another embodiment in which the receiver is adapted to receive magnetic field mode positional signals, the transmission of the reference signals from the signal generator 14 and the re-transmission of the positional signals from the wireless sensor/transmitter 12 may be time multiplexed. That is, each signal may engage a wireless communication channel for only a fraction of an interval on a periodic basis, so that they may jointly utilize the common channel on a time-shared basis. In so doing, the signals are kept apart so that they do not interfere with each other.

However, in the preferred embodiment of the receiver adapted to receive magnetic field mode positional signals, the frequency range of the positional signal is differed from the reference signal by a voltage-to-frequency converter within the sensor/transmitter so that time multiplexing is unnecessary, thereby avoiding loss of cycles of each signal and an accompanying reduced data rate. In this case, the device may receive continuous powering signals and reference signals from the signal generator.

Also in accordance with the present invention, there is provided an apparatus for locating a wireless sensor/ transmitter within an anatomical body including a processor for computing a position of the wireless sensor/transmitter as a function of the positional signals transmitted to the receiver. The processor may determine the position of the sensor/transmitter by solving equations representing signals induced in the sensing coil in response to a sequence of magnetic fields generated successively within the anatomical body. In the preferred embodiment of the present invention, the processor begins determining the position of the sensor/transmitter by first determining the angular orientation of the sensing coil and then using the orientation of the coil to further determine the position of the coil. However, as previously mentioned, the present invention is not limited to any specific method of determining the position of the wireless sensor/transmitter.

Another function of the processor may be to electrically activate the coil(s) of signal generator 14 to generate the desired electromagnetic fields. Yet another function of the processor may be to regulate the timing of the apparatus so that the processor may later recall which induced voltage corresponds to a given coil set within signal generator 14 when determining a position of the sensor/transmitter.

Also in accordance with the present invention, there is provided an apparatus for locating a wireless sensor/transmitter within an anatomical body including a circuit associated with the processor for outputting position image information to a display device. As embodied herein, the display device may include a display device 20, such as, for example, a CRT, LCD or other display suitable for displaying position image information for surgical procedures. The examples given are illustrative only. Display device 20 is not limited to any particular display.

FIG. 2 provides another example of a system environment wherein receiver 16, processor 18, and display device 20 are combined into an electromagnetic control unit 32. FIG. 2 illustrates how the electromagnetic control unit, or localizer, includes critical elements in determining the position of a wireless sensor/transmitter.

Figure 4:
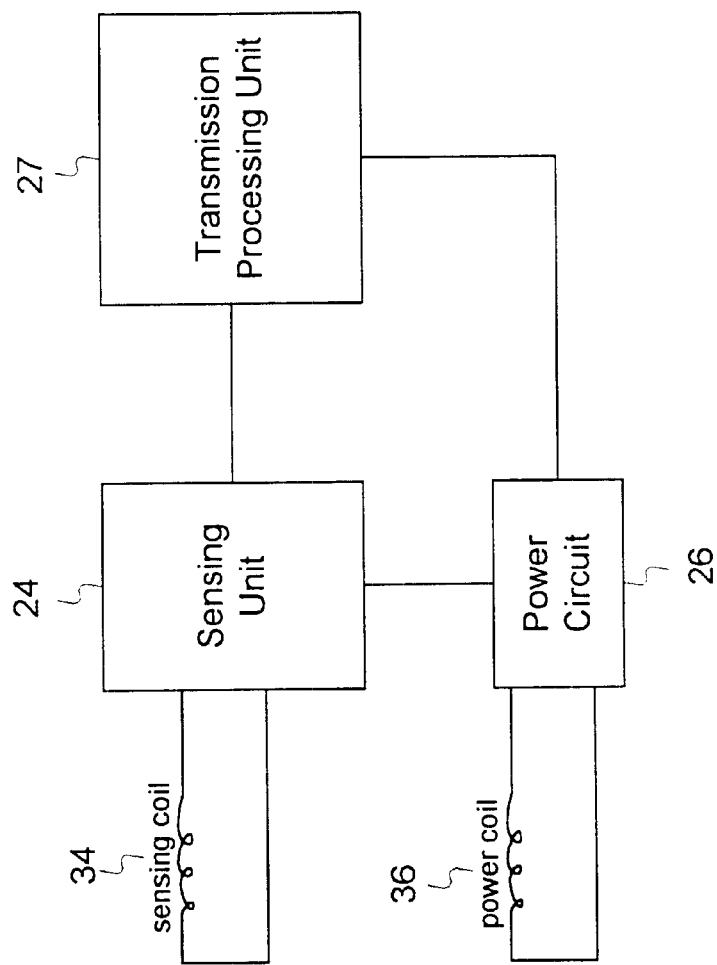

Also in accordance with the present invention, there is provided a wireless sensor/transmitter for use in surgical procedures to track the movement of structures within an anatomical body, such as organs and tissues, including a portion for receiving a reference signal from a reference signal generator. The portion for receiving a reference signal includes a coil adapted to have a voltage induced by the signal generator. For example, FIG. 4 illustrates a sensing coil 34 on which the reference signal may induce voltage corresponding to a positional signal indicative of a current position.

In a preferred embodiment of the invention, a sensing coil is not limited to receiving reference signals to induce voltage corresponding to positional signals. Instead, the sensing coil may also receive powering signals which induce sufficient voltage to power the transmitter. In the preferred embodiment of the device illustrated in FIGS. 2 and 3, sensing coil/power coil 22 induces voltage corresponding to both reference and positional signals from signal generator 14.

Figure 3:
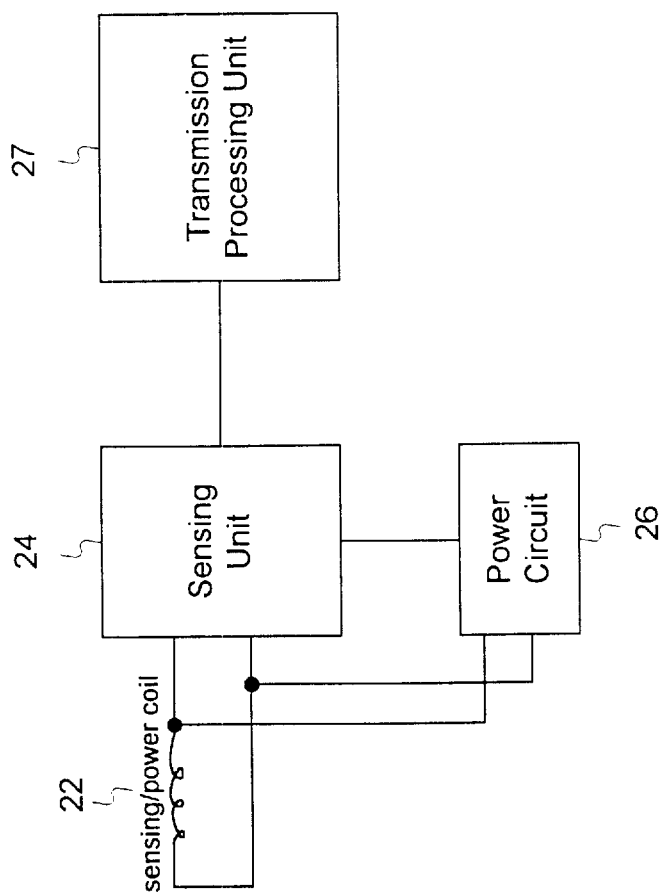
FIGS. 3–5 are schematic views of various embodiments of wireless sensor/transmitters in accordance with the invention.

As embodied herein, the portion for receiving a reference signal further includes a sensing unit and a powering circuit, such as sensing unit 24 and power circuit 26 shown in FIGS. 2 and 3. Sensing unit 24 and power circuit 26 of the preferred embodiment each may receive an induced voltage signal due to a frequency multiplexed reference signal and powering signal on sensing/powering coil 22. Sensing unit 24 and powering circuit 26 both may separate the voltage signals induced by the multiplexed magnetic signals into positional and powering signals. Standard frequency demodulating techniques are used for separating the signals.

Upon separation of the positional and powering signals, sensing unit 24 may measure the induced voltage signal portion corresponding to a reference signal as a positional signal indicative of a current position of a wireless sensor/transmitter 12. The positional signal is retained for further processing and re-transmission by a transmitting portion of the sensor/transmitter. Similarly, power circuit 26 may retain the induced voltage signal portion corresponding to a powering signal for use by the power circuit in producing power. Powering circuit 26 may rectify the induced voltage generated on a coil by the powering signals to produce DC power. Powering circuit 28 may store the DC power using a capacitor, small battery, or other storage means for later use by one or more components of the wireless sensor/transmitter. In a preferred embodiment, the DC power is produced continuously by powering circuit 26 and storage is not necessary.

In another embodiment shown in FIG. 4, separate coils are used for receiving, respectively, the reference signals and the powering signals. The processing performed by sensing unit 26 and power circuit 26 on the induced voltage signals corresponding to a frequency multiplexed reference signal and powering signal remain unchanged. Due to space constraints of the wireless sensor/transmitter, the aforementioned embodiment which utilizes a single coil in the system for powering the transmitter is preferred.

Also in accordance with the present invention, there is provided a wireless sensor/transmitter for use in surgical procedures to track the movement of structures within an anatomical body including a portion for wirelessly transmitting the reference signal as a positional signal indicative of a current position of the sensor. As illustrated in FIG. 2, the transmitting portion may include a transmission processing unit 27 that processes positional signals for transmission and then transmits the positional signals to a receiver.

Transmission processing unit 27 may include a voltage-to-frequency converter, embodied herein as voltage-to-frequency converter 28. Voltage-to-frequency converter 28 converts the induced voltage signal corresponding to the position of a wireless sensor/transmitter to a corresponding signal with a transmission frequency which is proportional to the measured voltage. The frequencies produced by the converter may be made to vary within a given range. Preferably, voltage-to-frequency converter 28 is powered by the rectifier circuit of power circuit 26. In other embodiments, however, a battery or other power source may power voltage-to-frequency converter 28.

Transmission processing unit 27 also may include a transmitter, embodied herein as transmitter 30. Transmitter 30, and hence transmission processing unit 27, may be configured for RF transmission or magnetic field transmission.

If RF transmission is employed, transmitter 30 may include an antenna to retransmit the positional signal to a receiver. The positional signal is preferably transmitted by the sensor/transmitter in the frequency range of 1 MHz to 1 GHz, where voltage-to-frequency converter 28 is adapted to produce the positional signal in the given frequency range according to the measured induced voltage. In the RF embodiment, as previously mentioned, transmitter 30 does not need to time-multiplex the re-transmission of positional signals with the transmission of reference signals since no interference between the signals occurs.

Figure 5:
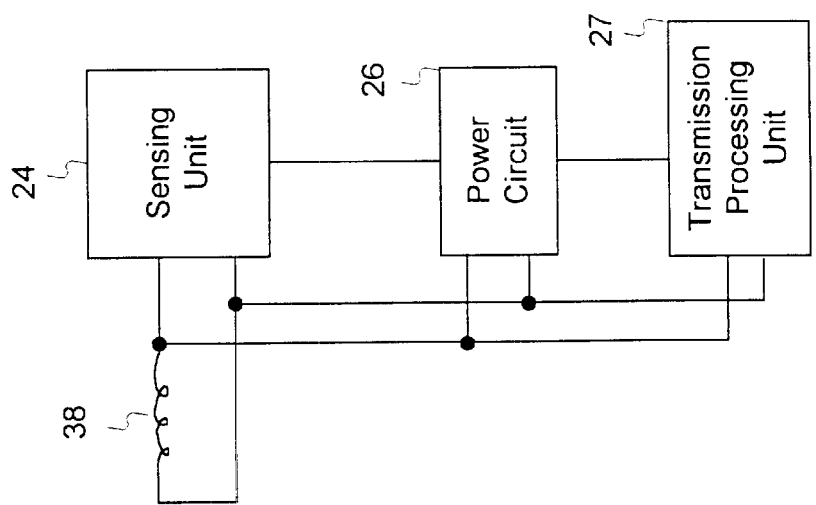

If magnetic field transmission is employed, transmitter 30 may include a coil arrangement to transmit the positional signal to the receiver. Transmitter 30 may have its own magnetic coil or it may share the coil of the sensing unit. As shown in FIG. 5, the transmitter may share a coil 38 that is used by both sensing unit 24 and power circuit 26. The positional signal is preferably transmitted by the sensor/transmitter in the frequency range of 50 KHz to 200 KHz. Using voltage-to-frequency converter 28 to produce the positional signal in the preferred frequency range according to the measured induced voltage, the system may multiplex the transmitted reference signal and re-transmitted positional signal in frequency, rather than in time. While another embodiment may be to time multiplex the reference and positional signals during magnetic field transmission, frequency multiplexing is preferred as it allows both signals to be transmitted simultaneously.

Alternatively, the transmitting portion of the wireless sensor/transmitter may include an inductor-capacitor (LC) tank circuit instead of a coil to transmit the positional signal via a magnetic field mode to the receiver. If an LC tank circuit is used instead of a coil for magnetic transmission of the positional signal, the LC tank circuit is tuned to a resonant frequency to receive the magnetic field and transmit it to the wireless magnetic receiver. As stated above, the position signal may have its frequencies changed from those of the reference signal to avoid time multiplexing during transmission, or it may use time multiplexing for simplification of the processing and transmission of the positional signal upon receiving the same.

The transmitting portion may also transmit the positional signal via digital RF transmission. If digital RF transmission is chosen, the transmission processing unit 27 may include an analog-to-digital (A/D) converter for converting the analog signal to digital. The A/D converter may include an A/D converter 40 shown in FIG. 6. The A/D converter 40 may be interfaced to a signal transmission module for direct transmission after conversion, or it may be interfaced to a digital signal processor (DSP) system for further processing.

Figure 6:
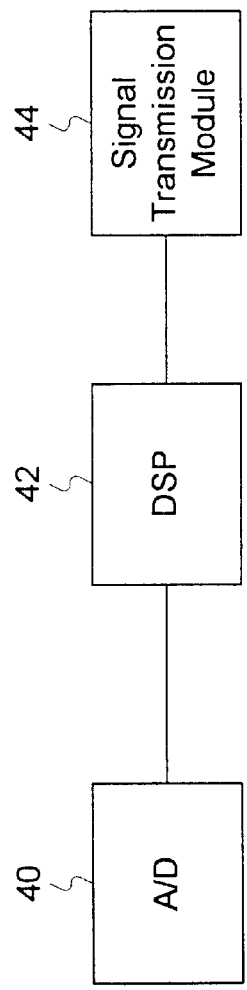
FIG. 6 is a schematic view of one embodiment of a transmitter in a wireless sensor/transmitter.

In a preferred embodiment illustrated in FIG. 6, the transmission processing unit further includes a DSP system 42. A DSP system allows for more effective use of the transmission bandwidth by processing the positional signal using conventional coding and compression techniques. The DSP system may be interfaced to a signal transmission module 44. Signal transmission module 44 of the present invention uses techniques similar to wireless modems or digital RF techniques to transmit the signal to the wireless receiver. In another embodiment, the DSP may be integrated with the A/D converter to conserve space. The A/D converter, DSP, and signal transmission module are preferably powered by power circuit 26. However, one or more of the above devices may be powered by a battery or other power source.

Other embodiments of the invention will be apparent to those skilled in the art from consideration of the specification and practice of the invention disclosed herein. For example, instead of using the induced voltage on the sensing coil to find the position of a wireless sensor/transmitter, one could induce voltage on a sensing coil of a probe to power any sensor or battery in the anatomical body. One sensor receiving power, for example, may be a thermostat for measuring temperature within the chamber of the heart.

Another embodiment of the invention may derive power in a wireless sensor/transmitter through an optical means. For example, the power coil of the present invention could be substituted with a photocell or solar cell to obtain optical power from an optical transmitter, such as infrared or a light-emitting diode (LED), and convert it to electrical power for use by the device. Moreover, any transmitter in the system may be substituted with an optical transmission means. Optical transmission means may be combined with other transmission means, such as magnetic or RF transmissions. For example, the sensing coil may receive electromagnetic signals for powering transmitter 30, while transmitter 30 may generate optical signals to receiver 16. The present invention allows various types of transmission It is intended that the specification and examples be considered as exemplary only, with a true scope and spirit of the invention being indicated by the following claims.

What is claimed is:

1. A surgical navigation apparatus for locating a wireless sensor/transmitter within an anatomical body during a surgical procedure, the apparatus comprising:

at least one signal generator remote from the anatomical body for sending reference signals through the anatomical body to be received by the sensor/transmitter and to be wirelessly re-transmitted by the sensor/transmitter as positional signals indicative of a current location of the sensor/transmitter within the anatomical body;

a receiver for receiving positional signals from the wireless sensor/transmitter;

a processor for computing a position of the wireless sensor/transmitter as a function of the positional signals transmitted to the receiver; and a circuit associated with the processor for outputting position image information to a display device.

2. The apparatus of claim 1, wherein the said at least one signal generator includes an electromagnetic field generator coil.

3. The apparatus of claim 2, wherein the sensor/transmitter includes a sensing coil and wherein the signal generator is configured to induce a voltage in the sensing coil sufficient to power a transmitting portion of the sensor/transmitter.

4. The apparatus of claim 1, wherein the receiver is adapted to receive RF mode positional signals transmitted by the sensor/transmitter.

5. The apparatus of claim 1, wherein the receiver is adapted to receive digital RF mode positional signals transmitted by the sensor/transmitter.

6. The apparatus of claim 1, wherein the receiver is adapted to receive magnetic field mode positional signals transmitted by the sensor/transmitter.

7. A wireless sensor/transmitter for use in surgical procedures to track the movement of structures within an anatomical body, comprising:

a portion for receiving a reference signal from a reference signal generator that is remote from the anatomical body; and a portion for wirelessly transmitting the reference signal as a positional signal indicative of a current position of the sensor.

8. The wireless sensor/transmitter of claim 7, wherein the receiving portion includes a coil adapted to have a voltage induced by the signal generator.

9. The wireless sensor/transmitter of claim 8 further including a circuit for powering the transmitter using the induced voltage.

10. The wireless sensor/transmitter of claim 7, wherein the transmitting portion includes a voltage to frequency converter.

11. The wireless sensor/transmitter of claim 10, wherein the transmitting portion further includes an antenna.

12. The wireless sensor/transmitter of claim 10, wherein the transmitting portion further includes a coil.

13. The wireless sensor/transmitter of claim 7, wherein the transmitting portion includes an A/D converter and a signal transmission module.

14. The wireless sensor/transmitter of claim 10, wherein the transmitting portion includes an LC tank circuit.

15. The wireless sensor/transmitter of claim 13, wherein the transmitting portion further includes a DSP for processing and compressing the positional signal to be transmitted.

16. A surgical navigation apparatus for navigating a surgical instrument within an anatomical body during a surgical procedure, said surgical navigation apparatus comprising:

a signal generator operable to transmit reference signals into the anatomical body from a site remote from the anatomical body; and a wireless sensor/transmitter attached to the surgical instrument, said wireless sensor/transmitter operable to receive said reference signals from said signal generator and operable to wirelessly transmit position signals indicative of a current location of the surgical instrument during the surgical procedure.

17. The surgical navigation apparatus as defined in claim 16 wherein said wireless sensor/transmitter further includes a coil operable to receive a signal from said signal generator to induce a voltage sufficient to power said wireless sensor/transmitter.

18. The surgical navigation apparatus as defined in claim 17 wherein said coil is both a sensing coil operable to sense said reference signals from said signal generator and a power coil operable to generate a voltage sufficient to power said wireless sensor/transmitter.

19. The surgical navigation apparatus as defined in claim 1 wherein said sensor/transmitter is attached to a surgical instrument.

20. The wireless sensor/transmitter as defined in claim 7 wherein said wireless sensor/transmitter is attached to a surgical instrument.

* * * * *

UNITED STATES PATENT AND TRADEMARK OFFICE
CERTIFICATE OF CORRECTION

PATENT NO. : 6,474,341 B1
DATED : November 5, 2002
INVENTOR(S) : Mark W. Hunter, Paul Kessman and Brad Jascob It is certified that error appears in the above-identified patent and that said Letters Patent is hereby corrected as shown below:

<u>Title page,</u>
Item [56], References Cited, U.S. PATENT DOCUMENTS, insert the following:

| | | |
|---|---|---|
| -- 5,711,299 | 01/27/98 | Manwaring et al. |
| 5,697,377 | 12/16/97 | Wittkampf |
| 5,694,945 | 12/9/97 | Ben-Haim |
| 5,682,886 | 11/4/97 | Delp et al. |
| 5,681,260 | 10/28/97 | Ueda et al. |
| 5,676,673 | 10/14/97 | Ferre et al. |
| 5,662,111 | 9/2/97 | Cosman |
| 5,647,361 | 7/15/97 | Damadian |
| 5,638,819 | 6/1797 | Manwaring et al. |
| 5,630,431 | 5/20/97 | Taylor |
| 5,622,170 | 4/22/97 | Schultz |
| 5,622,169 | 4/22/97 | Golden et al. |
| 5,617,857 | 4/8/97 | Chader et al. |
| 5,603,318 | 2/18/97 | Heilbrun et al. |
| 5,592,939 | 1/14/97 | Martinelli |
| B1 5,383,454 | 12/31/96 | Bucholz |
| 5,568,809 | 10/29/96 | Ben-Haim |
| 5,558,091 | 9/24/96 | Acker et al. |
| 5,546,951 | 8/20/96 | Ben-Haim |
| 5,515,160 | 5/7/96 | Schultz et al. |
| 5,494,034 | 2/27/96 | Schlöndorff et al. |
| 5,483,961 | 1/16/96 | Kelly et al. |
| 5,480,422 | 1/2/96 | Ben-Haim |
| 5,456,718 | 10/10/95 | Szymaitis |
| 5,453,686 | 9/26/95 | Anderson |
| 5,445,150 | 8/29/95 | Dumoulin et al. |
| 5,443,489 | 8/22/95 | Ben-Haim |
| 5,443,066 | 8/22/95 | Dumoulin et al. |
| 5,425,382 | 6/20/95 | Golden et al. |
| 5,425,367 | 6/20/95 | Shapiro et al. |
| 5,391,199 | 2/21/95 | Ben-Haim |
| 5,383,454 | 1/24/95 | Bucholz |
| 5,377,678 | 1/3/95 | Dumoulin et al. |
| 5,359,417 | 1/25/94 | Müller et al. |
| 5,353,807 | 10/11/94 | DeMarco |

UNITED STATES PATENT AND TRADEMARK OFFICE
CERTIFICATE OF CORRECTION

PATENT NO.    : 6,474,341 B1
DATED         : November 5, 2002
INVENTOR(S)   : Mark W. Hunter, Paul Kessman and Brad Jascob It is certified that error appears in the above-identified patent and that said Letters Patent is hereby corrected as shown below:

U.S. PATENT DOCUMENTS, cont'd,
| | | |
|---|---|---|
| 5,353,795 | 10/11/94 | Souza et al. |
| 5,332,971 | 6/26/94 | Aubert |
| 5,318,025 | 6/7/94 | Dumoulin et al. |
| 5,305,203 | 4/14/94 | Raab |
| 5,271,400 | 12/21/93 | Dumoulin et al. |
| 5,265,610 | 11/30/93 | Darrow et al. |
| 5,261,404 | 11/16/93 | Mick et al. |
| 5,255,680 | 10/26/93 | Darrow et al. |
| 5,253,647 | 10/19/93 | Takahashi et al. |
| 5,251,127 | 10/5/93 | Raab |
| 5,243,984 | 9/14/93 | Ogura et al. |
| 5,211,165 | 5/18/93 | Dumoulin et al. |
| 5,458,123 | 10/1995 | Unger |
| 5,262,772 | 11/1993 | Urbas et al. -- |

Column 6,
Line 31, "sensing unit 26" should be -- sending unit 24 --.

Signed and Sealed this

Twelfth Day of August, 2003

JAMES E. ROGAN
*Director of the United States Patent and Trademark Office*